US 7,491,548 B2

(12) United States Patent
Quine et al.

(10) Patent No.: US 7,491,548 B2
(45) Date of Patent: Feb. 17, 2009

(54) METHOD AND DEVICE FOR COLLECTING AND TRANSFERRING BIOHAZARD SAMPLES

(75) Inventors: Douglas B. Quine, Bethel, CT (US); Ashwani Sharma, West Haven, CT (US); John E. Massucci, Eastchester, NY (US)

(73) Assignee: Pitney Bowes Inc., Stamford, CT (US)

( * ) Notice: Subject to any disclaimer, the term of this patent is extended or adjusted under 35 U.S.C. 154(b) by 1087 days.

(21) Appl. No.: 10/741,264

(22) Filed: Dec. 19, 2003

(65) Prior Publication Data

US 2005/0135973 A1    Jun. 23, 2005

(51) Int. Cl.
    *G01N 33/00* (2006.01)
(52) U.S. Cl. .................. 436/177; 422/50; 422/68.1; 422/69; 422/83; 422/88; 422/100; 422/101
(58) Field of Classification Search ............ 422/50, 422/68.1, 69, 83, 88, 99, 100, 101; 436/177
See application file for complete search history.

(56) References Cited

U.S. PATENT DOCUMENTS

| | | | |
|---|---|---|---|
| 4,069,965 A | 1/1978 | Maddox, Jr. ............... 232/19 |
| 5,099,679 A | 3/1992 | Huerlimann et al. ....... 73/19.06 |
| 5,368,226 A | 11/1994 | Franceschino ............ 232/19 |
| 5,429,803 A * | 7/1995 | Guirguis .................. 422/58 |
| 6,324,927 B1 | 12/2001 | Ornath .................. 73/864.33 |
| 6,463,815 B1 * | 10/2002 | Tallentire et al. .......... 73/863.23 |
| 6,740,836 B2 | 5/2004 | Ryan ...................... 209/584 |
| 6,742,703 B2 | 6/2004 | Esakov ................... 232/45 |
| 6,789,727 B2 | 9/2004 | Felice .................... 232/44 |
| 7,060,927 B1 | 6/2006 | Quine et al. .............. 209/584 |
| 2003/0074987 A1 | 4/2003 | Dalmia et al. ............. 73/864 |
| 2003/0155412 A1 | 8/2003 | Felice .................... 232/45 |
| 2003/0209595 A1 | 11/2003 | Felice |
| 2005/0008533 A1 | 1/2005 | Avant .................... 422/28 |
| 2005/0136540 A1 | 6/2005 | Quine et al. .............. 436/1 |

FOREIGN PATENT DOCUMENTS

| | | |
|---|---|---|
| EP | 1366696 A2 | 3/2003 |
| GB | 1067166 | 5/1967 |
| GB | 2303111 A | 2/1997 |
| WO | 03/054778 A1 | 7/2003 |
| WO | 03/058207 A2 | 7/2003 |

* cited by examiner

*Primary Examiner*—Jill Warden
*Assistant Examiner*—Samuel P Siefke
(74) *Attorney, Agent, or Firm*—George M. Macdonald; Angelo N. Chaclas (57) ABSTRACT

A method and system for collecting airborne particles and hydrating the collected particles for analysis. The airborne particles, which may be biological contaminants, are collected from a container containing one or more mailpieces. In the collection stage, a dry filter collection assembly is connected to the container and air is drawn out of the container through a dry filter. A hydration solution is then injected into the collection assembly to hydrate the collected particles. Part of the hydration solution containing the collected particles is caused to move out of the collection assembly to a test cartridge for further testing.

11 Claims, 10 Drawing Sheets

Figure 1:
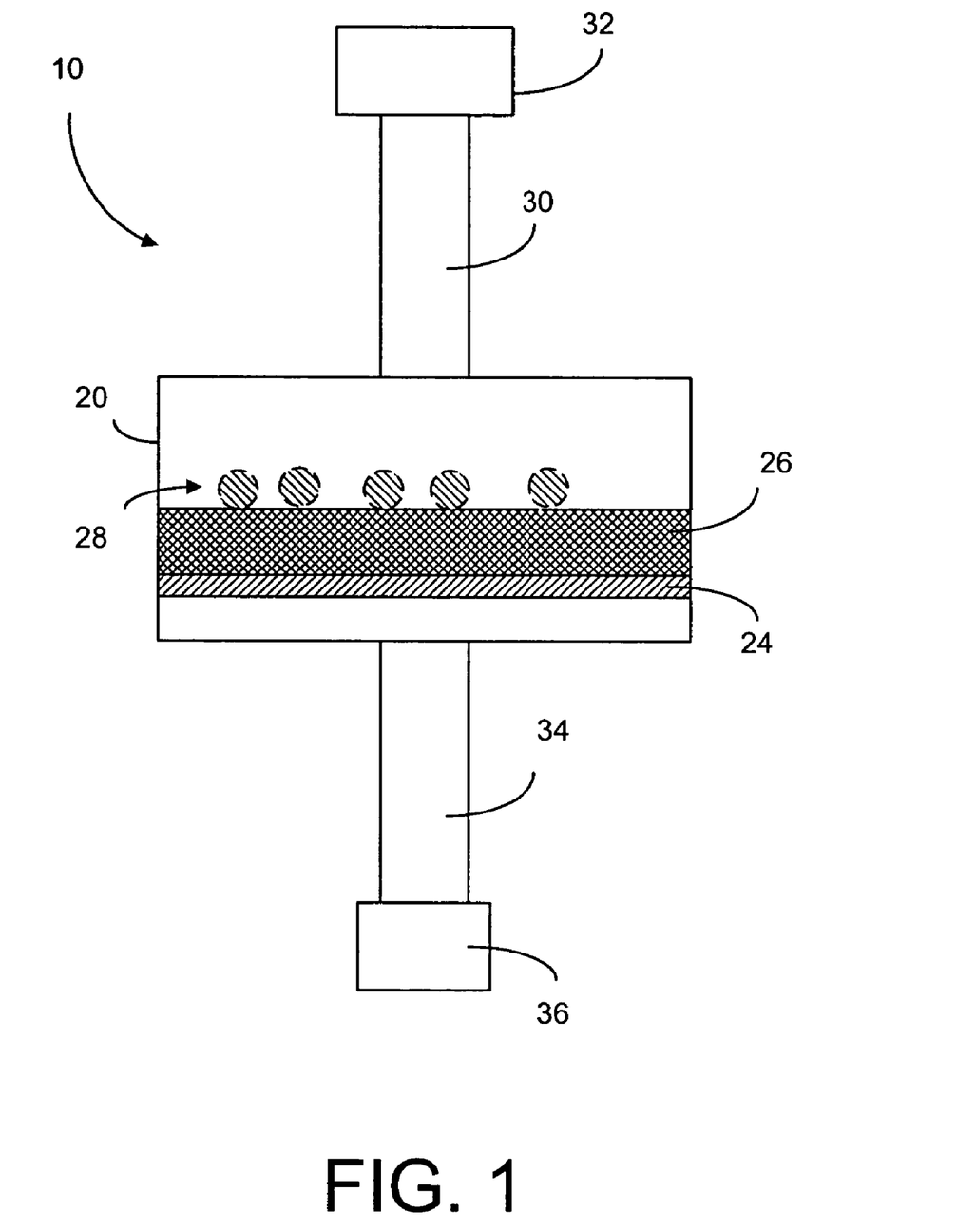
Figure 2:
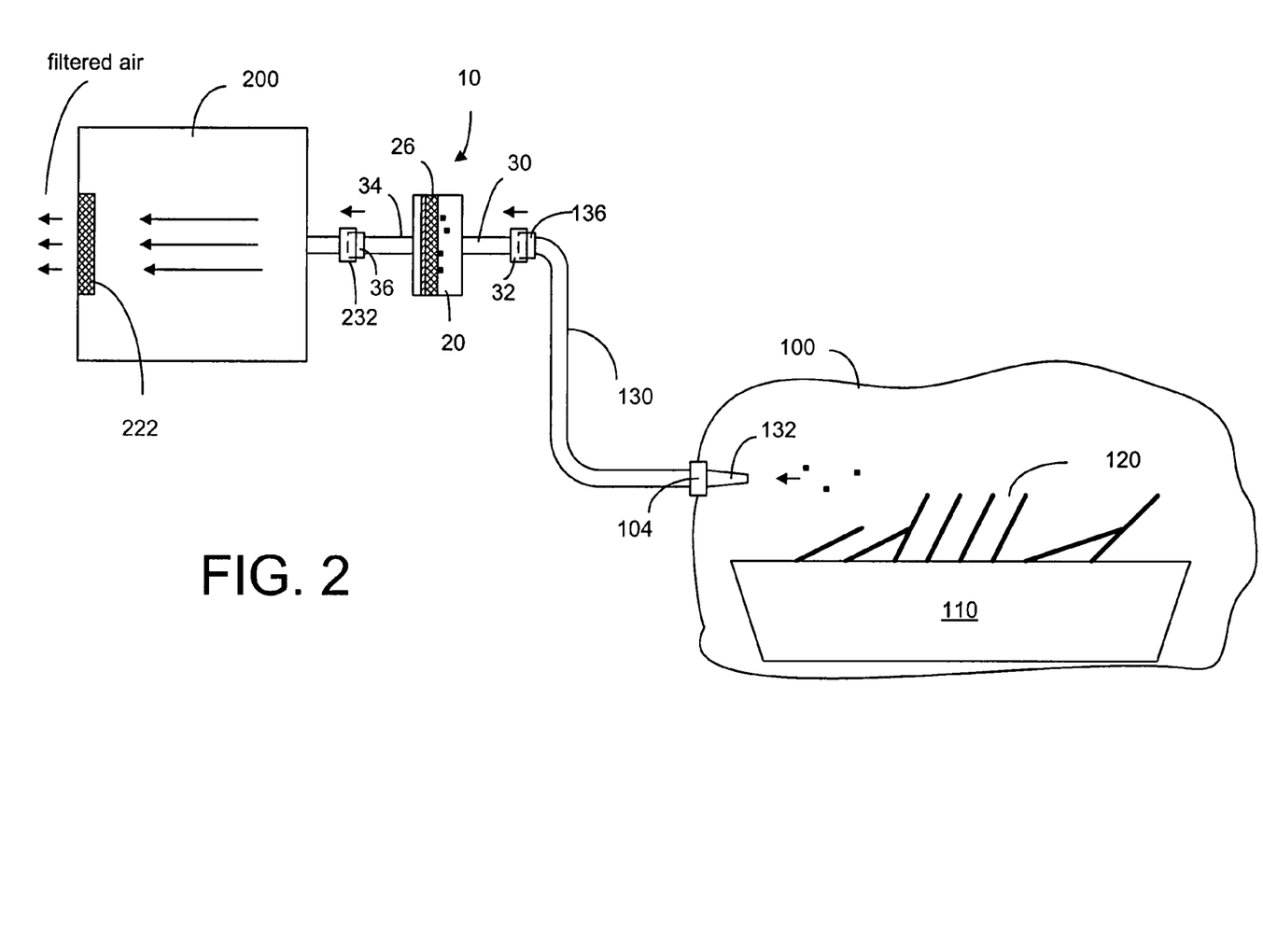

Alternatively, they are of different shapes or sizes. The filter chamber may optionally contain a plurality of beads 28, as described later in conjunction with the agitation process. In the contaminant collection process, the first passageway 30 of the collection assembly 10 is operatively connected to a mailbag 100, which contains a mail tray 110 having one or more mailpieces 120. As shown in FIG. 2, the mailbag 100 has a tubing 130. One end of the tubing 130 is securely affixed to a self-sealed coupler 136. The other end of the tubing has an open inlet 132 to allow air to be drawn out from the mailbag 100 through the filter chamber 20 of the collection assembly 10, when the coupler 136 is engaged with the coupler 32. The open inlet 132 may be shaped like a "T" or have a number of orifices so that there are multiple sub-inlets to prevent blockage of air flow in the event that the end of the inlet touches the inner walls of the mailbag 100. The second passageway 34 of the collection assembly 10 is operatively connected to an air pump system 200 so as to allow air to be drawn out from the filter chamber 20 through an air filter 222, when the coupler 36 is engaged with a coupler 232 on the air pump system 200. It should be noted that the pores on the filter 222 should be small enough to prevent biological contaminants from passing through. For example, the filter 222 is a HEPA filter. Prior to or during the collection process, it would be advantageous to disturb the mailpieces 120 so as to cause the contaminants contained within the mailpieces to be released outside, or to cause the contaminants attached on the mailpieces to be dislodged and aerosolized. For example, the mailpieces can be disturbed by shaking the tray or by dropping the tray from a height of one foot. Preferably, the mailbag 100 is made of an anti-static material so that the released or dislodged contaminants do not become attached to the interior of the mailbag 100. When the coupler 136 and the coupler 32 are disconnected from each other, each of the couplers 136, 32 becomes self sealed. Likewise, when the coupler 36 and the coupler 232 are disconnected from each other, each of the couplers 36 and 232 becomes self-sealed. Thus, when the collection assembly 10 is disconnected from the mailbag 100 and the air pump system 200, the collection assembly 10 is sealed at both first and second passageways 30, 34. Thus, the collected contaminants in the filter chamber 20 are prevented from being released to the surroundings. Likewise, the coupler 136 is sealed, preventing the contaminants in the mailbag 100 from being released into the air. As for the air pump system 200, only the coupler 232 becomes self-sealed. Air can still pass through the filter 222. However, any unexpected contaminants collected inside the air pump system 200 are prevented from passing through the filter 222.

Figure 3A:
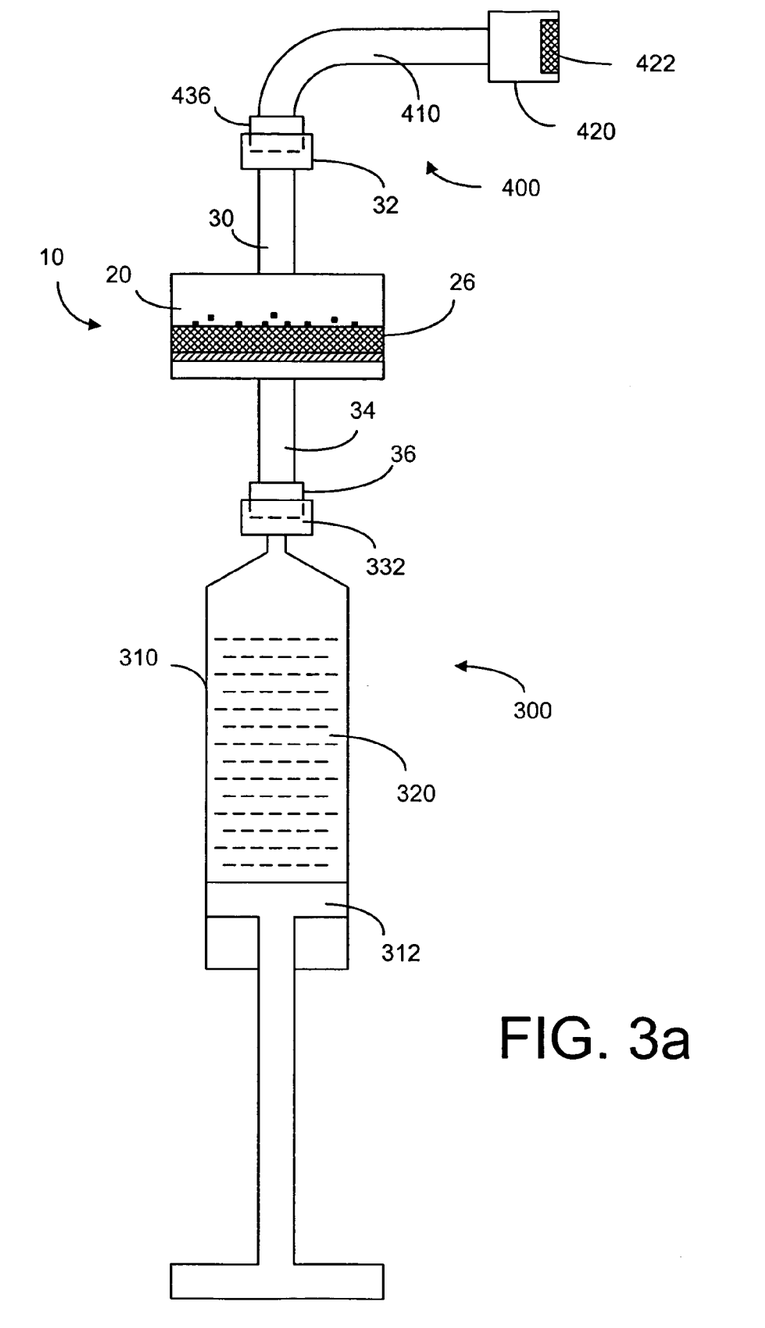
Figure 3B:
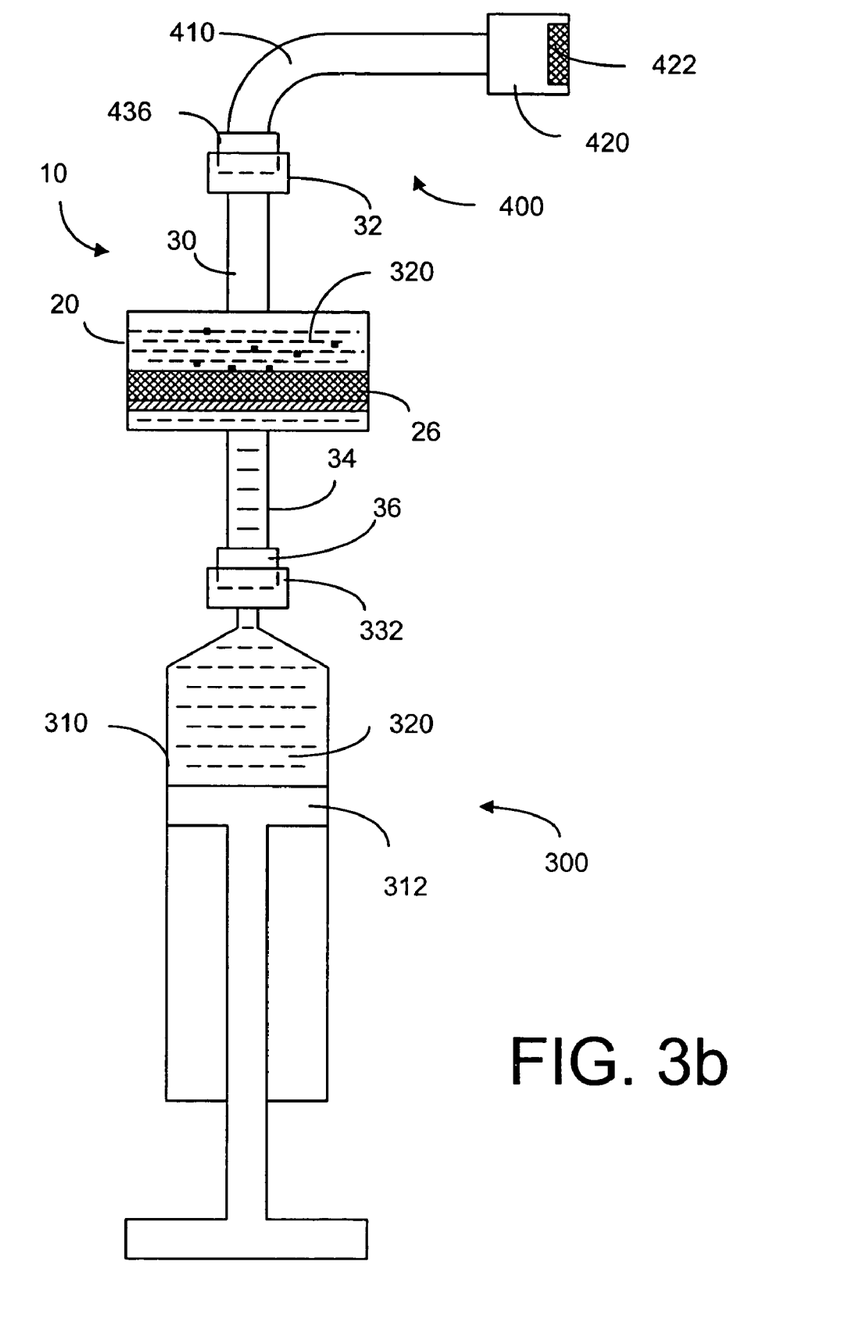

In the hydration process, the collection assembly 10 that has been disconnected from the mailbag 100 and the air pump system 200 is connected to a liquid injection system 300, as shown in FIG. 3a. The liquid injection system 300 has a liquid containing body 310 securely connected to a coupler 332, which can be engaged with the second coupler 36 of the collection assembly 10. For example, the liquid containing body 310 can be a syringe for injecting a desirable amount of hydration solution 320 backward into the filter chamber 20 through the second passageway 34 in order to flush the collected particles out of the filter 26 and into fluid suspension. On the other end of the collection assembly 10, the first passageway 30 is securely connected to a filter system 400 so as to allow the air inside the filter chamber 20 to be released when the hydration solution 320 is injected into the filter chamber 20. The filter assembly 400 is made of a tubing 410 having a coupler 436 on one end and a filter holder 420 on the other end. The filter holder 420 is used to support a HEPA filter 422 or the like. The coupler 436 is also self-sealed, but it can be engaged with the first coupler 32 so as to allow the air in the collection assembly 10 to exit through the tubing 410 and then the filter 422. Preferably, in the hydration process, the collection assembly 10 is only partially filled with the hydration solution 320 from the liquid containing body 310, as shown in FIG. 3b. For example, while the syringe is filled with a hydration solution, the plunger 312 is only partially depressed. As such, the remaining hydration solution can be used later in the transfer stage. At this stage, it is desirable to agitate the collection system 10 to cause the contaminants retained by the filter 26 to mix with the hydration solution in the filter chamber 20. Agitation can be carried out in many ways. For example, it is possible to place the edge of a vortex head in a vortex device in contact with the collection system 10 so as to allow the vortex head to shake the collection system 10 for 10 seconds, for example. Further, it may be desirable to preload or introduce a plurality of glass or plastic beads 28 into the filter chamber 20, as shown in FIG. 1, so that these beads can help dislodge the contaminants from the filter 26 during agitation.

Figure 4:
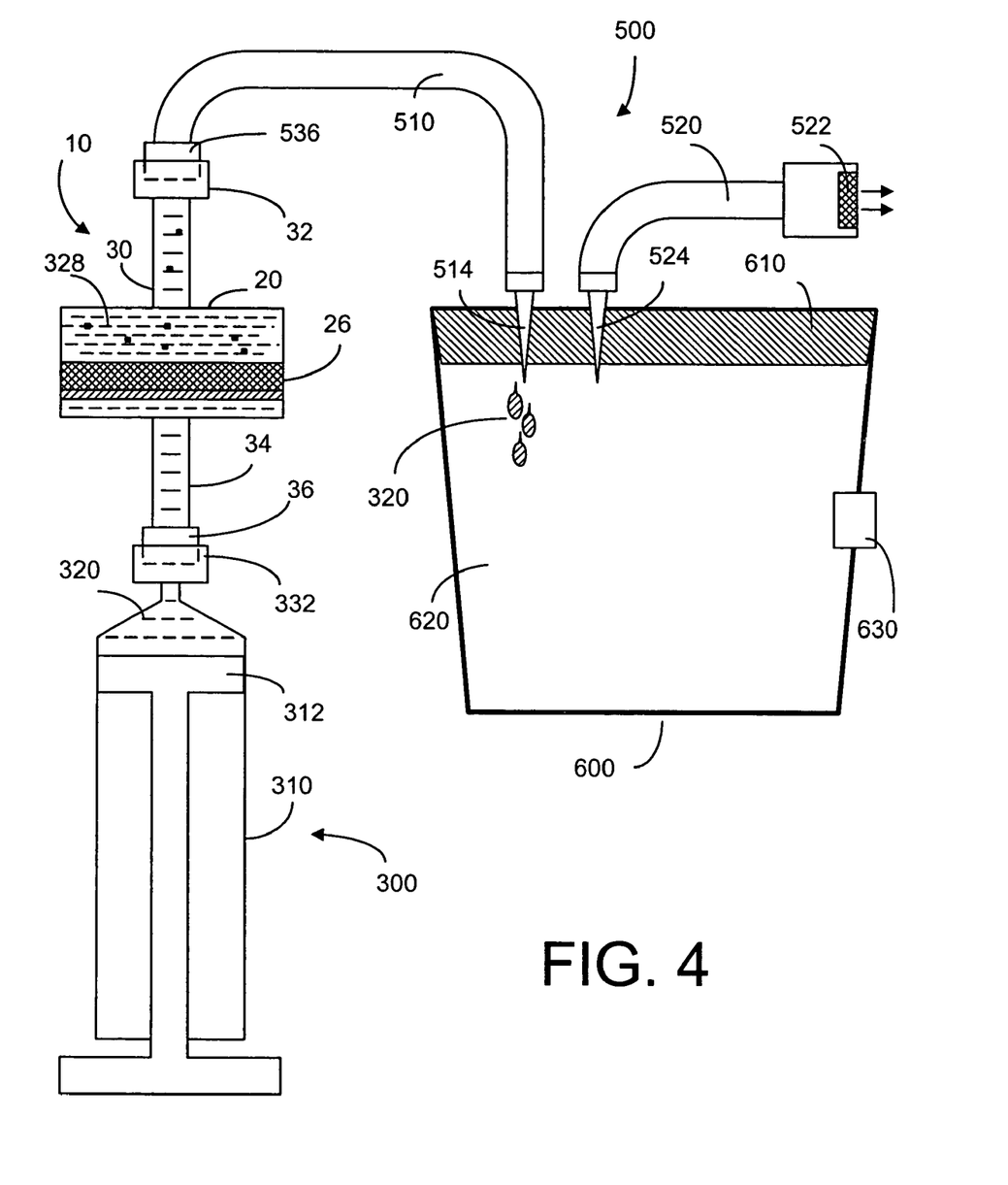

After agitation, the filter assembly 400 is removed from the collection assembly 10. A transfer system 500 is used to transfer part of the hydration solution 320 in the filter chamber 20 to a test cartridge 600, which contains the chemistry 620 for PCR analysis. Preferably, the test cartridge 600 comprises a septum cover 610 for sealing the cartridge. The septum 610 allows an injection needle to puncture through. But when the needle is pulled off the septum, the septum becomes self-sealed. It should be noted that, in this transfer stage, the contaminants within the collection assembly 10 are in contact with a liquid. Thus, aerosolization of the biological contaminants is substantially avoided. As shown in FIG. 4, the transfer system 500 comprises an injection needle 514 connected to one end of a tubing 510, and a coupler 536 is connected to the other end. The transfer system 500 also comprises an air-venting needle 524 connected to one end of another tubing 520, and an air filter 522 connected to the other end. After the injection needle 514 and the air-venting needle 524 are adequately inserted into the test cartridge 600 through the septum cover 610, more hydration solution is injected into the collecting assembly 10 in order to push part of the hydration solution 320 inside the filter chamber 20 into the test cartridge 600. The displaced air is filtered by filter 522 to prevent release of any contaminants into the room. Before removing the test cartridge 600 from the transfer 500 so that the test cartridge can be placed in a test device for contaminant detection, it is preferable to withdraw the remaining liquid in the needle 514, the tubing 510 and the coupler 536 by backing off the syringe 300.

It should be noted that the test cartridge 600 for PCR analysis contains a plurality of separate chemical chambers for carrying out PCR processes. Thus, the injection needle 514 must be inserted through the septum cover 610 in the correct position so that the hydration solution is injected into the correct chamber. It is possible that the transfer system 500 has a keyed shape that fits the test cartridge only in a certain way so as to ensure the needle 514 punctures the septum in the correction position. Moreover, if the amount of hydration solution injected into the cartridge 600 is small, it may not be necessary to provide the air-venting needle 524 for air venting as long as the injection does not result in pressurizing the system. In an alternative embodiment, the transfer system 500 is also to preload the necessary chemical solutions into the test cartridge 600. One or more additional needles may be positioned on the transfer system 500 to introduce the chemical solutions into the chemical reaction chambers or to puncture the sealed bladders within these chemical reaction chambers for releasing the chemical solutions preloaded in the bladders.

Figure 5:
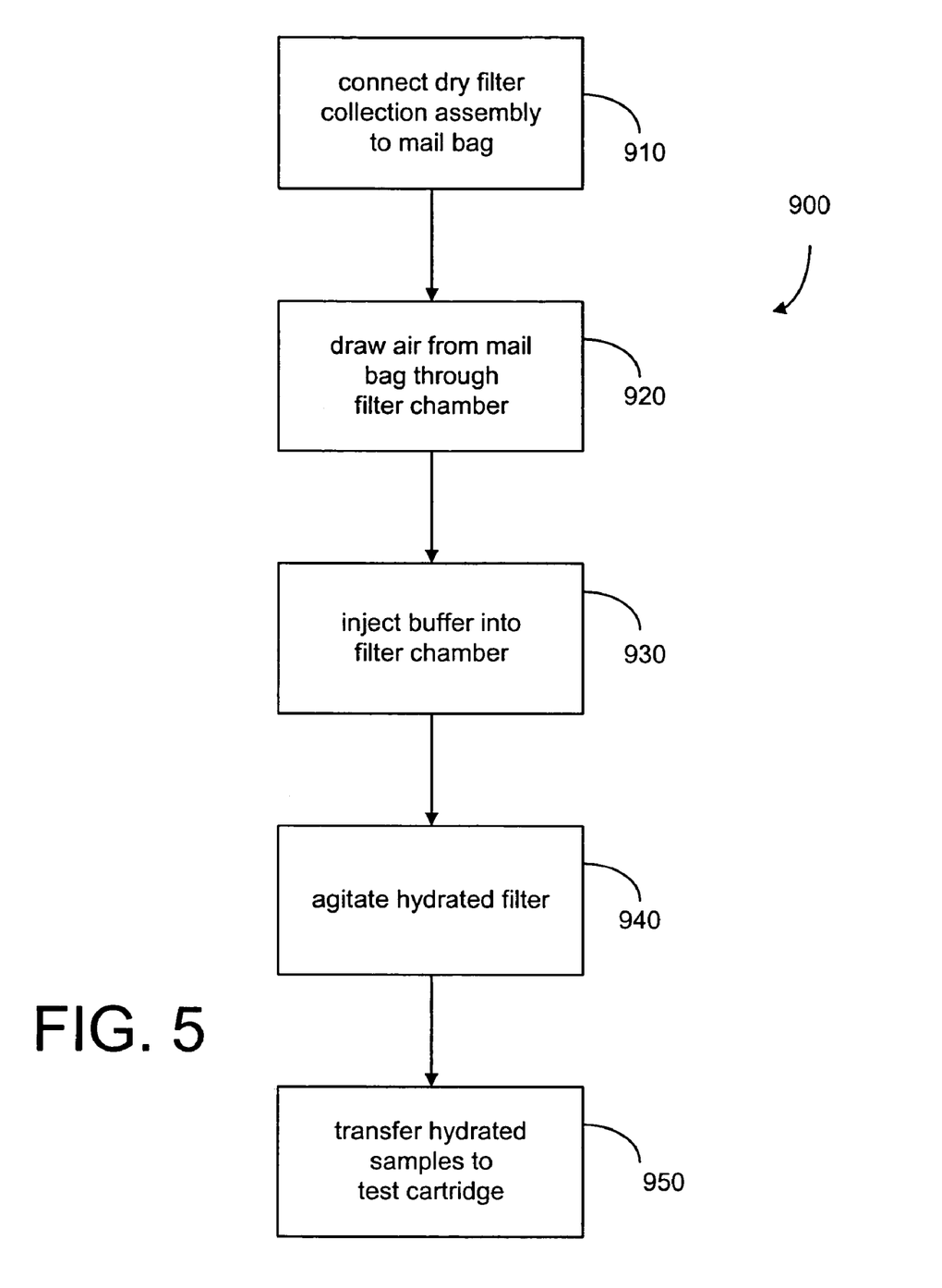

In sum, the method of collecting contaminants from a container such as mailbag and transferring the collected contaminants to a test cartridge, according to the present invention, is illustrated in the flowchart 900 in FIG. 5. As shown, a dry filter collection assembly 10 is connected to a mailbag 100 at step 910. The dry filter collection assembly 10 is also connected to an air pump system 200 so as to allow air in the mailbag to be drawn through the filter collection assembly 10 at step 920. After the filter collection assembly 10 is disconnected from the mailbag, a hydration solution is injected into the filter collection assembly at step 930. The filter collection assembly 10 is agitated, at step 940, in order to suspend at least part of the collected contaminants in the hydration solution. Finally, more liquid is injected into the filter collection assembly, at step 950, in order to push some of the hydration solution containing the contaminants into the test cartridge.

It should be noted that many components in the collection/ transferring device, according to the present invention, are available as off-the-shelf products. For example, the dry filter collection assembly 10 can be modified from a filter cassette (Omega A0037503) supplied by BGI (Waltham, Mass.). The filter 26 is an Omega M083700P filter supplied by BGI. The filter is 37 mm MCE (mixed cellulose ester) 0.8 micron filter with a backing pad. This filter has been shown to capture substantially all anthrax spores. The coupler 32 is a self-seal male connector and the coupler 36 is a self seal female connector (62860-288 connector pair) made by VWR International (West Chester, Pa.) or PLCD170412 and mate made by Colder Products Corp (St. Paul, Minn.). The mailbag 100 is an aegis pink 36"×42"×0.004 anti-static poly bag with amines, Part No. 3508 supplied by Marathon Plastics, Inc. (Shelton, Conn.). The filter 222 is HEPA filter made by Whatman, Inc. (Clifton, N.J.). The test cartridge 600 is a 4 plex anthrax test cartridge made by Cepheid (Sunnyvale, Calif.) for use in a GeneXpert PCR 4-channel test system made by Cepheid. However, these products can be substituted by equivalents.

It should be noted that when the hydration solution is injected into the filter collection assembly at step 930, it is desirable that the amount of injected hydration solution is predetermined such that the filter chamber 20 is only partially filled. As such, the hydration solution in the filter chamber 20 can be easily agitated with a vortex device or the like. Accordingly, it is desirable to have a marking, indicative of the predetermined amount, provided on the syringe so that the person who depresses the plunger knows when to stop depressing the plunger. It is possible that a stopping device is used to limit the depressing of the plunger when needed. It is also possible to use two different syringes to provide a liquid to the filter chamber: one in the hydrating step and the other in the transferring step. It is also possible to move part of the hydration solution containing the particles out of the filter chamber to the test cartridge by injecting air into the filter chamber through the second passageway 34.

Figure 6A:
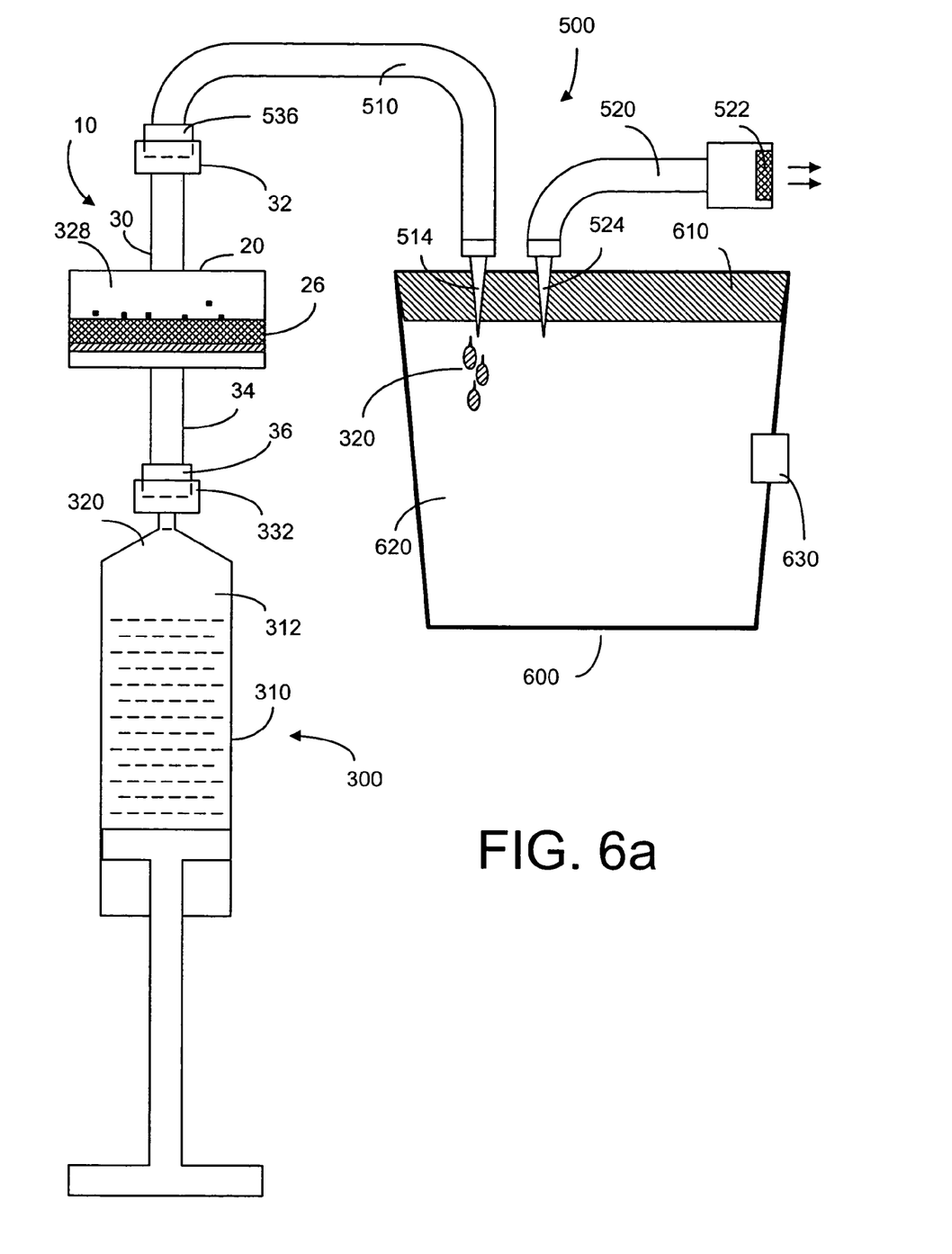
Figure 6B:
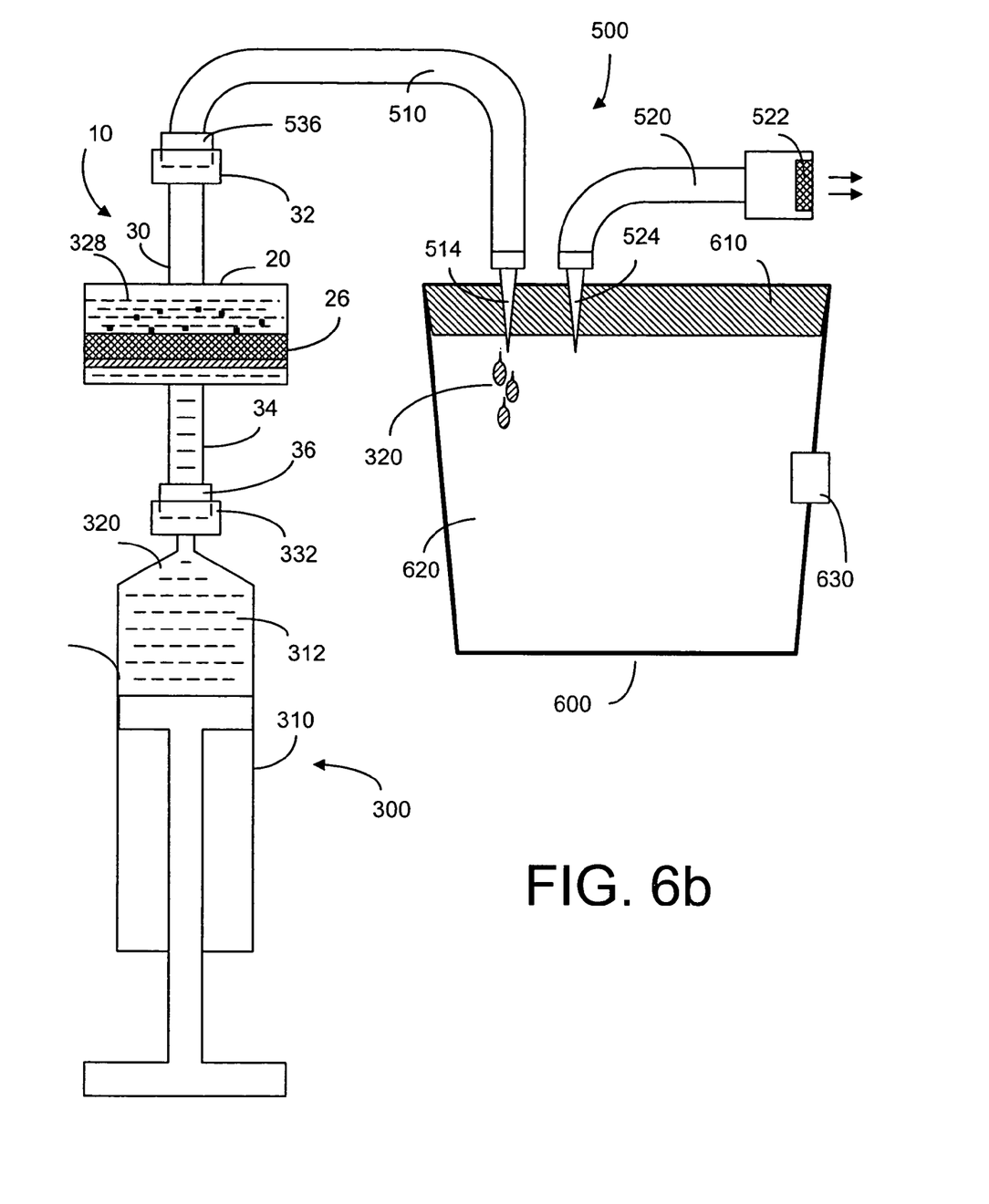

In a different embodiment, the transfer system 500 is securely attached to the test cartridge 600 as an integral part thereof. It is also possible that before the liquid injection system 300 is used to inject the hydration solution into the filter chamber 20, the first passageway 30 is directly connected to the transfer system 500 with the coupler 32 engaged with the coupler 536, as shown in FIG. 6a. The collection assembly 10 is then partially filled with the hydration solution 320, as shown in FIG. 6b. After the filter chamber 20 is agitated to further dislodge the collected particles from the filter 26, additional solution is injected into the collection assembly in order to push part of the hydration solution 320 inside the filter chamber 20 into the test cartridge 600, as shown in FIG. 4. The hydration solution can be distilled water or a buffer solution.

In another embodiment, the collection assembly 10 and the transfer system are integrated with the test cartridge 600 as a single functional unit, thereby eliminating the need for many of the self-sealing couplers. While the Cepheid GeneXpert System is designed for use with stand alone test cartridges, a low profile transfer device 500 could be attached on top of the test cartridge 600 and left in place as it is placed into the analysis device. Thin tubes and structural connections could be aligned to exit through the gaps around the GeneExpert door (or the door could be removed/modified) so that the collection, transfer, and test device could remain as a single sealed unit even during sample analysis.

Figure 7:
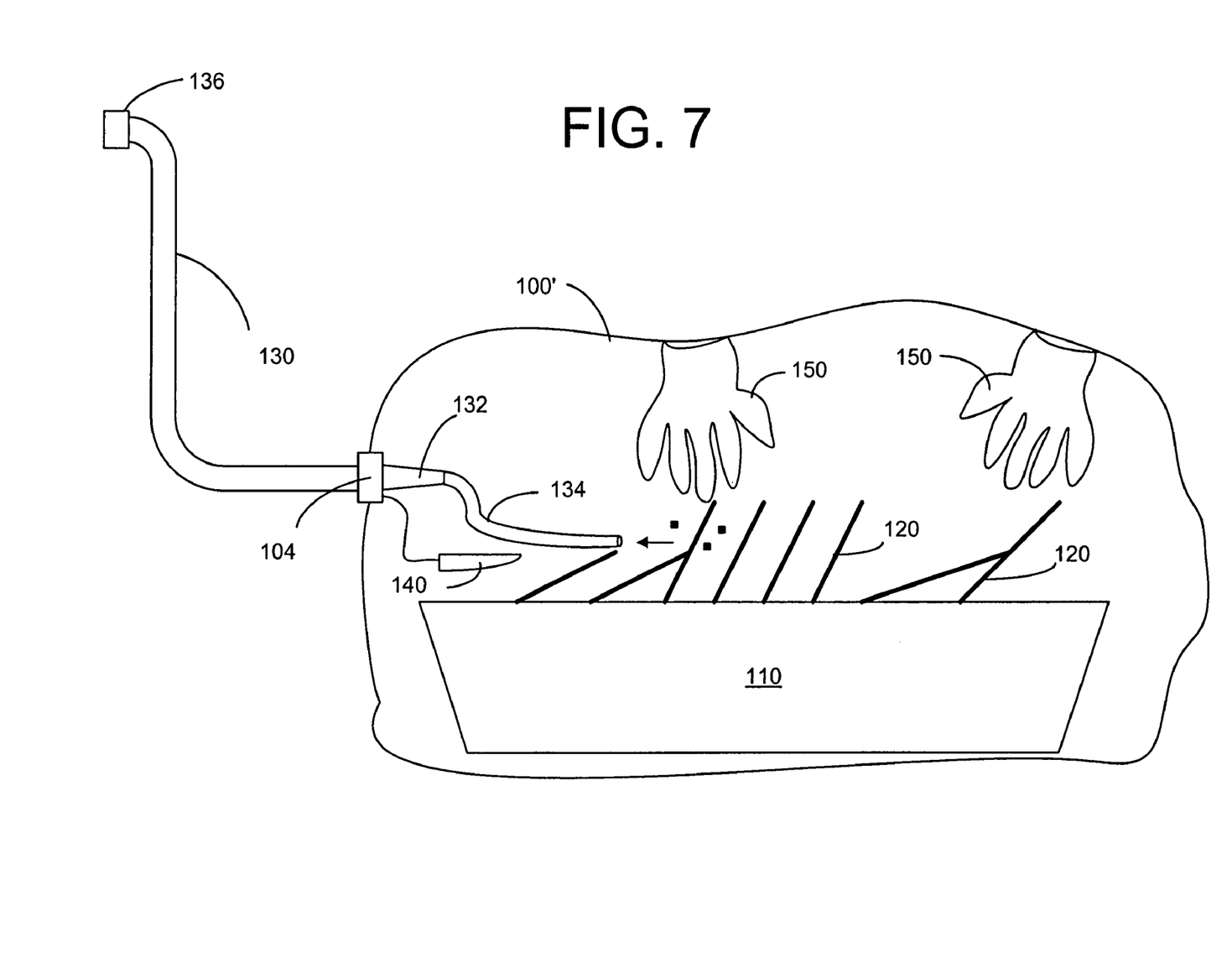

It is possible that the mailbag 100' is a glove bag having a pair of gloves 150 so as to allow a person to access the mailpieces 120 inside the bag 100' through the gloves, as shown in FIG. 7. A flexible tube 134 is extended from the inlet 132 so that it can be inserted into each of the mailpieces 120 for directly collecting particles in individual mailpieces. It is also possible to provide a cutter 140 inside the mailbag 100' to make a small slit cut on the mailpieces so as to allow the flexible tube 134 to be inserted into the slit cut.

Figure 8:
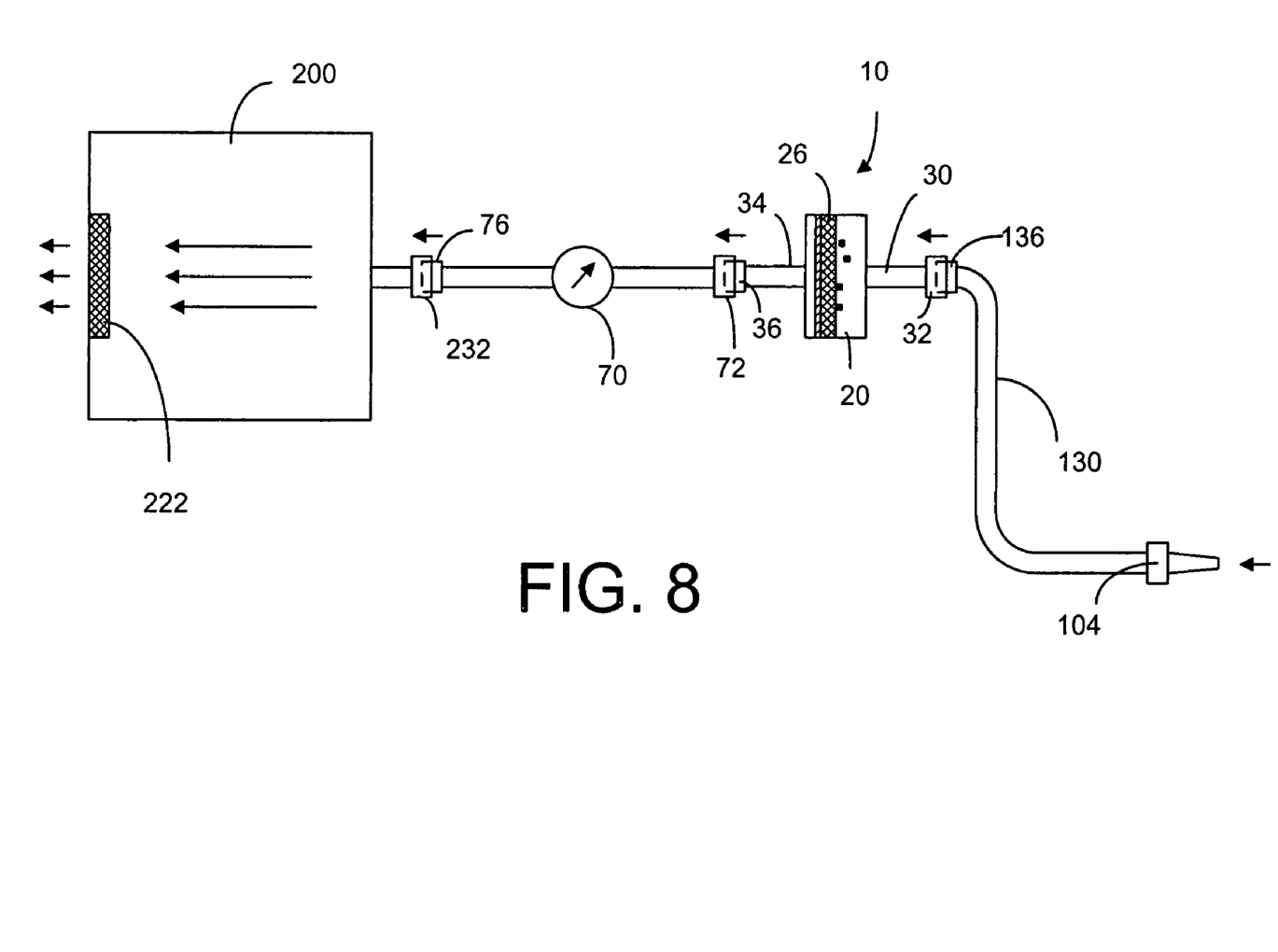

It is advantageous to install a flow gauge in the filter collection assembly to monitor the air flow. For example, an air flow gauge 70 having couplers 72 and 76 is installed between the air pump system 200 and the collection assembly 10, as shown in FIG. 8. The air flow gauge 70 could be a valuable element in that it provides a confirmation that air is being successfully sampled from the mailbag 100. The gauge 70 also provides objective demonstration of the air flow rate (6 liters per minute, for example). If the air flow is blocked, this may indicated that the tubing is kinked, the mailbag has been completely evacuated, or the self-sealing couplers are not properly engaged. For example, flow gauge 20 SCFH with tube fittings from King Instrument Company (Garden Grove, Calif.) can be used for such purposes. The air flow gauge may provide audio indication that the flow is not normal.

It should be also noted that the filter collection system, according to the present invention, allows for the creation of a sample volume greater than that required for a single test run so that the same sample can be used for re-testing if needed.

Thus, although the invention has been described with respect to a preferred embodiment thereof, it will be understood by those skilled in the art that the foregoing and various other changes, omissions and deviations in the form and detail thereof may be made without departing from the scope of this invention.

What is claimed is:

1. A particle collecting and transferring system for collecting particles that may be contaminants in the air in a container at a first operations stage and transferring the collected particles to a test cartridge at a second operations stage, said system comprising:

a collection assembly having a filter chamber, a first passageway extended from the filter chamber, the first passageway having a first coupler, and a second passageway extended from the filter chamber, the second passageway having a second coupler; and a liquid providing device connectable to the collection assembly, wherein at the first stage, the first coupler is used to operatively connect the filter chamber to the container so as to draw at least part of the air in the container through the first passageway, the filter chamber and then the second passageway for collecting in the filter chamber the particles in the air, and at the second stage, the second coupler is used to operatively connect the filter chamber to the liquid providing device so as to allow the liquid providing device to provide a liquid to the filter chamber through the second passageway for hydrating in the filter chamber the collected particles, and the first coupler is used to operatively connect the filter chamber to the test cartridge so as to transfer at least part of the liquid in the filter chamber containing the hydrated particles through the first passageway to the test cartridge, wherein the liquid in the filter chamber is agitated in said hydrating, said system further comprising, a plurality of beads disposed in the filter chamber for said agitating.

2. The system of claim 1, wherein the second coupler is connected to an air drawing device so as to allow the air drawing device to draw said at least part of the air in the container at the first stage.

3. The system of claim 2, wherein the second coupler is disconnected from the air drawing device before the second coupler is connected to the liquid providing device for providing the liquid at the second stage.

4. The system of claim 3, wherein the second coupler seals off the second passageway after the second coupler is disconnected from the air drawing device so as to substantially prevent the collected particles from leaking out of the filter chamber through the second passageway.

5. The system of claim 4, wherein the second coupler opens the second passageway after the second coupler is connected to the liquid providing device so as to allow the liquid providing device to provide the liquid at the second stage.

6. The system of claim 1, wherein the first coupler is disconnected from the container before the first coupler is connected to the test cartridge for transferring said at least part of the liquid to the test cartridge.

7. The system of claim 6, wherein the first coupler seals off the first passageway after the first coupler is disconnected from the container so as to substantially prevent the collected particles from leaking out of filter chamber through the first passageway.

8. The system of claim 7, wherein the first coupler opens the first passageway after the first coupler is connected to the test cartridge for transferring said at least part of the liquid to the test cartridge.

9. A particle collecting and transferring system for collecting particles that may be contaminants in the air in a container at a first operations stage and transferring the collected particles to a test cartridge at a second operations stage, said system comprising:

a collection assembly having a filter chamber, a first passageway extended from the filter chamber, the first passageway having a first coupler, and a second passageway extended from the filter chamber, the second passageway having a second coupler; and a liquid providing device connectable to the collection assembly, wherein at the first stage, the first coupler is used to operatively connect the filter chamber to the container so as to draw at least part of the air in the container through the first passageway, the filter chamber and then the second passageway for collecting in the filter chamber the particles in the air, and at the second stage, the second coupler is used to operatively connect the filter chamber to the liquid providing device so as to allow the liquid providing device to provide a liquid to the filter chamber through the second passageway for hydrating in the filter chamber the collected particles, and the first coupler is used to operatively connect the filter chamber to the test cartridge so as to transfer at least part of the liquid in the filter chamber containing the hydrated particles through the first passageway to the test cartridge, wherein said liquid providing device comprises a syringe, the syringe having a syringe body for holding the liquid;

a discharging end extended from the syringe body;

a coupler securely affixed to the discharging end for connecting the liquid providing device to the collection assembly at the second stage; and a plunger, engaged with the syringe body, for moving at least part of the liquid in the syringe body through the discharging end for providing the liquid to the filter chamber at the second stage, wherein the amount of the liquid provided to the filter chamber for hydrating the collected particles is predetermined, and wherein the syringe body has a marking indicative of the predetermined amount.

10. A particle collecting and transferring system for collecting particles that may be contaminants in the air in a container at a first operations stage and transferring the collected particles to a test cartridge at a second operations stage, said system comprising:

a collection assembly having a filter chamber, a first passageway extended from the filter chamber, the first passageway having a first coupler, and a second passageway extended from the filter chamber, the second passageway having a second coupler; and a liquid providing device connectable to the collection assembly, wherein at the first stage, the first coupler is used to operatively connect the filter chamber to the container so as to draw at least part of the air in the container through the first passageway, the filter chamber and then the second passageway for collecting in the filter chamber the particles in the air, and at the second stage, the second coupler is used to operatively connect the filter chamber to the liquid providing device so as to allow the liquid providing device to provide a liquid to the filter chamber through the second passageway for hydrating in the filter chamber the collected particles, and the first coupler is used to operatively connect the filter chamber to the test cartridge so as to transfer at least part of the liquid in the filter chamber containing the hydrated particles through the first passageway to the test cartridge, wherein the second coupler is connected to an air drawing device so as to allow the air drawing device to draw said at least part of the air in the container at the first stage, further comprising an air flow gauge, disposed in relation to the air drawing device, for monitoring a flow rate of said at least part of the air drawn from the container.

11. The system of claim 9, wherein the syringe is also used to provide a further amount of liquid to the filter chamber for moving said at least part of the liquid in the filter chamber to the test cartridge in said transferring.

* * * * *